United States Patent
Deamer

(10) Patent No.: US 7,772,390 B1
(45) Date of Patent: Aug. 10, 2010

(54) LIPID MEDIATED NUCLEIC ACID SYNTHESIS

(75) Inventor: David W. Deamer, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 337 days.

(21) Appl. No.: 11/880,111

(22) Filed: Jul. 18, 2007

Related U.S. Application Data

(60) Provisional application No. 60/831,780, filed on Jul. 18, 2006.

(51) Int. Cl.
C07H 21/00 (2006.01)

(52) U.S. Cl. .................... 536/25.3; 536/22.1; 536/23.1; 536/23.4

(58) Field of Classification Search ........................ None
See application file for complete search history.

(56) References Cited

U.S. PATENT DOCUMENTS

| | | | |
|---|---|---|---|
| 5,547,835 | A | 8/1996 | Koster |
| 5,948,902 | A | 9/1999 | Honkanen et al. |
| 6,599,284 | B2 | 7/2003 | Faour |
| 6,607,878 | B2 | 8/2003 | Sorge |
| 6,632,645 | B1 | 10/2003 | Gu et al. |
| 6,635,463 | B2 | 10/2003 | Ma et al. |
| 6,673,616 | B1 | 1/2004 | Dahlberg et al. |
| 6,677,146 | B1 | 1/2004 | Janjic et al. |
| 6,692,917 | B2 | 2/2004 | Neri et al. |
| 6,696,250 | B1 | 2/2004 | Cech et al. |
| 6,699,979 | B2 | 3/2004 | Cook |
| 6,706,471 | B1 | 3/2004 | Brow et al. |
| 6,706,474 | B1 | 3/2004 | Lu et al. |
| 6,709,815 | B1 | 3/2004 | Dong et al. |
| 6,753,169 | B2 | 6/2004 | Hess et al. |
| 6,759,226 | B1 | 7/2004 | Ma et al. |
| 6,762,022 | B2 | 7/2004 | Makarov et al. |
| 6,767,703 | B2 | 7/2004 | Schumm et al. |
| 6,780,982 | B2 | 8/2004 | Lyamichev et al. |
| 6,783,940 | B2 | 8/2004 | McLaughlin et al. |
| 6,825,009 | B2 | 11/2004 | Stanton, Jr. et al. |
| 6,852,487 | B1 | 2/2005 | Barany et al. |
| 6,870,026 | B1 | 3/2005 | Dean |
| 6,872,816 | B1 | 3/2005 | Hall et al. |
| 6,875,572 | B2 | 4/2005 | Prudent et al. |
| 6,890,719 | B2 | 5/2005 | Lu et al. |
| 6,893,819 | B1 | 5/2005 | Sorge |
| 6,913,881 | B1 | 7/2005 | Aizenstein et al. |
| 6,992,180 | B1 | 1/2006 | Engelhardt et al. |
| 7,045,289 | B2 | 5/2006 | Allawi et al. |
| 7,045,319 | B2 | 5/2006 | Hanna |
| 7,060,436 | B2 | 6/2006 | Lyamichev et al. |
| 7,060,440 | B1 | 6/2006 | Kless |
| 7,063,945 | B2 | 6/2006 | Seela et al. |
| 7,067,643 | B2 | 6/2006 | Dahlberg et al. |
| 7,078,499 | B2 | 7/2006 | Odedra et al. |
| 7,083,917 | B2 | 8/2006 | Barany et al. |
| 7,087,381 | B2 | 8/2006 | Dahlberg et al. |
| 7,101,672 | B2 | 9/2006 | Dong et al. |
| 7,118,860 | B2 | 10/2006 | Sorge et al. |
| 7,135,312 | B2 | 11/2006 | Kool |
| 7,141,377 | B2 | 11/2006 | Gelfand et al. |
| 7,150,982 | B2 | 12/2006 | Allawi et al. |
| 7,166,688 | B1 | 1/2007 | Dean |
| 7,183,052 | B2 | 2/2007 | Sorge |
| 7,189,508 | B2 | 3/2007 | Sorge et al. |
| 7,192,708 | B2 | 3/2007 | Lu et al. |
| 7,195,871 | B2 | 3/2007 | Lyamichev et al. |
| 7,198,893 | B1 | 4/2007 | Koster et al. |
| 7,211,654 | B2 | 5/2007 | Gao et al. |
| 7,214,522 | B2 | 5/2007 | Gu et al. |
| 7,226,738 | B2 | 6/2007 | Hanna |
| 7,238,795 | B2 | 7/2007 | Seela et al. |

FOREIGN PATENT DOCUMENTS

WO   WO94/21822 A1   9/1994

OTHER PUBLICATIONS

Flynn-Charlebois et al. J. Am. Chem. Soc. (2003), vol. 125, pp. 5346-5350.*
Treyer et al. Langmuir (2002), vol. 18, pp. 1043-1050.*
Schneega et al. Reviews in Molecular Biotechnology (2001), vol. 82, pp. 101-121.*
Ferris et al., "Montmorillonite catalysis of RNA oligomer formation in aqueous solution. A model for the prebiotic formation of RNA," J Am. Chem. Soc., 1993, 115:12270-12275.
Hasan et al., "Base-boronated dinucleotides: synthesis and effect of N7-cyanoborane substitution on the base protons," Nucleic Acids Res., 1996, 24(11):2150-2157.
Huang et al., "Synthesis of 35-40 mers of RNA oligomers from unblocked monomers. A simple approach to the RNA world," Chem. Commun., 2003, 21:1458-1459.
Inoue et al., "A nonenzymatic RNA polymerase model," Science, 1983, 219(4586):859-862.
Li et al., "Boron-containing oligodeoxyribonucleotide 14mer duplexes: enzymatic synthesis and melting studies," Nucleic Acids Res., 1995, 23(21):4495-4501.
Nakamaye et al., "Direct sequencing of polymerase chain reaction amplified DNA fragments through the incorporation of deoxynucleoside alpha-thiotriphosphates," Nucleic Acids Res., 1988, 16(21):9947-9959.

* cited by examiner

*Primary Examiner*—Patrick T Lewis
(74) *Attorney, Agent, or Firm*—Bret E. Fleid; Bozicevic, Field & Francis, LLP

(57) ABSTRACT

Methods and compositions for synthesizing polymers, such as nucleic acids, are provided. Aspects of the invention include methods in which lipids and monomeric precursors, e.g., mononucleotides, of the desired polymeric products are combined to produce a reaction mixture. The reaction mixture is then subjected to one or more steps of drying and rehydrating to produce a desired polymeric product, e.g., nucleic acid. Also provided are the polymeric products themselves, e.g., nucleic acid products, as well as systems and kits for practicing embodiments of the invention.

20 Claims, 4 Drawing Sheets

LIPID MEDIATED NUCLEIC ACID SYNTHESIS

CROSS-REFERENCE TO RELATED APPLICATION

Pursuant to 35 U.S.C. §119 (e), this application claims priority to the filing date of U.S. Provisional Application No. 60/831,780 filed Jul. 18, 2006, the disclosure which is herein incorporated by reference in its entirety.

INTRODUCTION

Nucleic acids find use in a variety of different applications including, but not limited to, research reagents, diagnostic agents and therapeutic agents. A variety of different protocols have been developed to synthesize nucleic acids. However, there is continued interest in the identification of new ways to synthesize nucleic acid.

Non-enzymatic nucleic acid synthesis has been studied. This includes anhydrous heating of nucleotides (Verlander et al., *J. Mol. Evol.* (1973) 2:303), cycles of heating and drying (Usher, D. A. *Science* (1977) 196:311), as well as studying the impact of amphiphilic structures (Walde, P. *Orig Life Evol Biosph*. Apr. 27 (2006) (E-publication ahead of print); Deamer, D. W. and G. L. Barchfeld. (1982) *J. Mol. Evol.* 18:203; and Szostak J. W., Bartel, D. P. and Luisi, P. L. *Nature* (2001) 409:387).

Condensation of activated mononucleotides also has been employed for non-enzymatic synthesis. Imidazole esters of mononucleotides assemble on RNA templates to produce complementary RNA strands up to 40-50 nucleotides in length (Inoue T, and Orgel, L. E. *Science* (1983) 219:859; and Orgel, L. *Orig. Life Evol. Biosphere* (1997) 28:227). Mineral surfaces of montmorillonite clay organize imidazole-activated mononucleotides and synthesize RNA strands up to 50-mers in the absence of templates (Huang, W. and Ferris J. P. *Chem. Commun.* (2003) 21:1458; and Ferris, *J. Orig. Life Evol. Biosphere* (2002) 32:311). RNA oligomers of up to 14 nucleotides in length spontaneously assemble in the absence of templates or organizing surfaces when activated mononucleotides are concentrated in the eutectic phase of frozen reaction mixtures (Kanavarioti et al., *Astrobiology* (2002) 1:271).

Unfortunately, synthesis of nucleic acids as reported above has met with limited success. To this end, there is a need for new ways to synthesize nucleic acid employing non-enzymatic strategies. The present invention addresses this and other needs.

SUMMARY

Methods and compositions for synthesizing polymers, e.g., nucleic acids or other polymers, are provided. Aspects of the invention include methods in which lipids and monomeric precursors e.g., mononucleotides, of the desired polymeric product are combined to produce a reaction mixture. The reaction mixture is then subjected to one or more steps of drying and rehydrating to produce a desired polymeric product, e.g., a nucleic acid, such as an RNA. Also provided are the polymeric products, e.g., nucleic acid products, produced by the present invention, as well as systems and kits for practicing embodiments of the invention.

BRIEF DESCRIPTION OF THE FIGURES

The file of this patent contains at least one drawing executed in color. Copies of this patent with color drawings will be provided by the Patent and Trademark Office upon request and payment of the necessary fee.

FIG. 3A shows the result of varying the number of cycles from 1 to 7. Several controls are also shown. Lane A: air was used instead of carbon dioxide during drying (7 cycles). Lane B: Lipid absent (7 cycles). Lane C: unheated control. Lane D: 10 μg of commercial polyadenylic acid as positive control for the end labeling process. Lane E shows an RNA ladder containing known lengths of RNA in 10 nt increments. The effects of varying temperature (3B), lipid (3C), mononucleotide to lipid ratio (3D), mixtures of mononucleotide (3E) and enzymatic hydrolysis (3F) were also investigated. (See text for details.) The abbreviations for lipid are POPC (1-palmitoyl-2-oleoylphosphatidylcholine) POPA (1-palmitoyl-2-oleoylphosphatidic acid) and LPC (egg lyso-phosphatidylcholine). The abbreviations for mononucleotide (AMP, 5'-adenosine monophosphate; UMP, 5'-uridine monophosphate) also indicate which lipid was used and the mole ratio of mononucleotide to lipid.

DEFINITIONS

Figure 1:
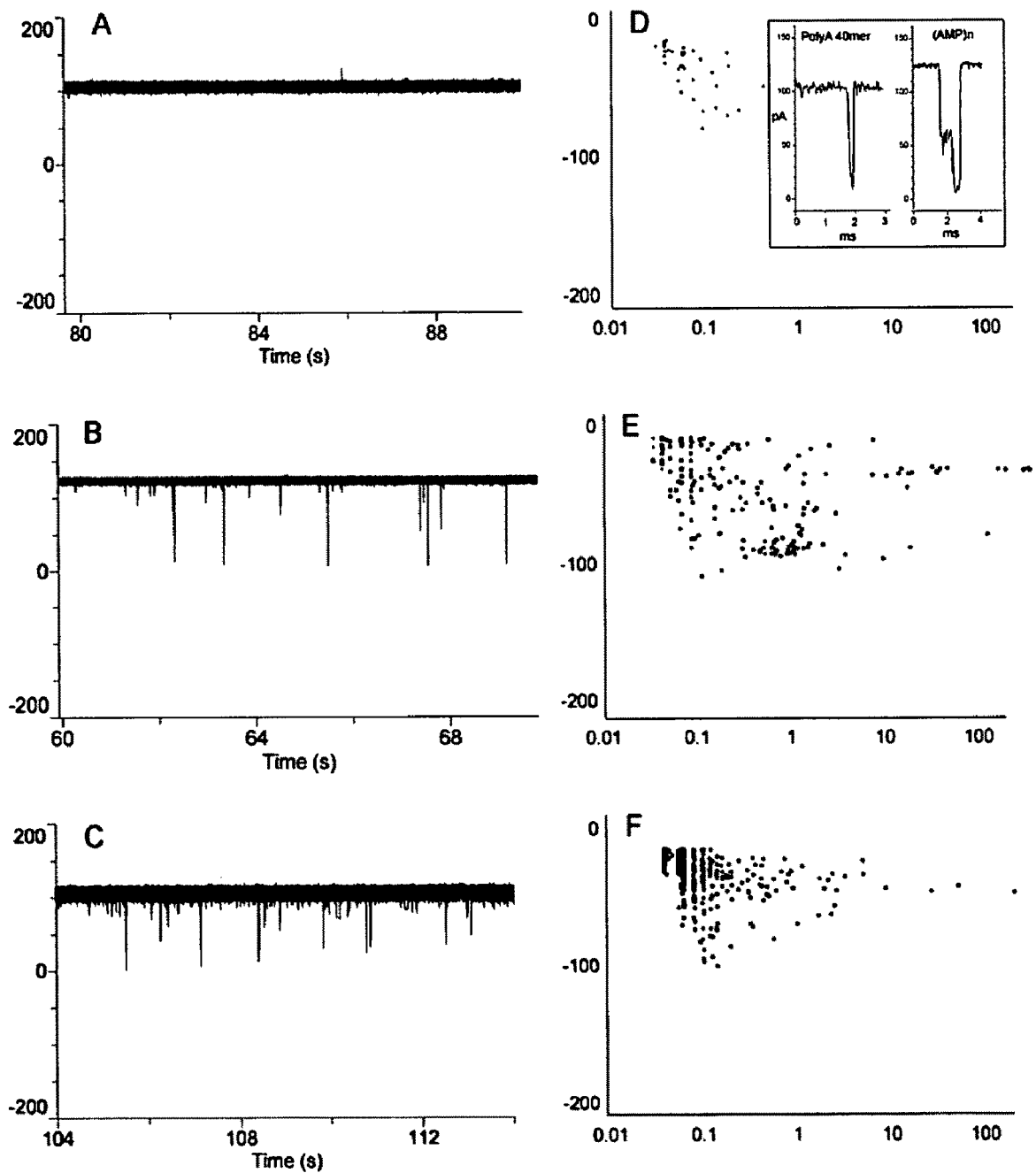
FIG. 1. Nanopore analysis of RNA products. A: open channel current through a hemolysin nanopore. B: blockades produced by a known 40 mer of polyadenylic acid; C: blockades produced by the RNA-like product from AMP:POPC after 5 cycles. D, E and F show corresponding event diagrams in which blockade amplitude in picoamps is plotted against blockade duration in milliseconds. Each point represents the amplitude and duration of a single polymer molecule as it is translocated through the pore by an applied voltage of 120 mV. D: Open channel current, no additions. A few short-lived low amplitude events seen in the control run of three minutes duration (D) are of unknown origin. The inset in D shows examples of individual blockade events produced by a polyA 40 mer and the product. Numerous blockades are produced by the known 40 mer (E). Blockades were also observed when the RNA-like product was added (F) which indicate the presence of linear RNA-like polymers.

The term "monomer" as used herein refers to a chemical entity that can be covalently linked to one or more other such entities to form a polymer. In certain embodiments, the monomers are nucleotide "monomers" that have first and second sites (e.g., 5' and 3' sites) suitable for binding to other like monomers by means of standard chemical reactions (e.g., nucleophilic substitution), and a diverse element which distinguishes a particular monomer from a different monomer of the same type (e.g., a nucleotide base, etc.). In the art synthesis of nucleic acids of this type utilizes an initial substrate-bound monomer that is generally used as a building-block in a multi-step synthesis procedure to form a complete nucleic acid.

The terms "nucleoside" and "nucleotide" are intended to include those moieties which contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like.

The term "polymer" means any compound that is made up of two or more monomeric units covalently bonded to each other, where the monomeric units may be the same or different, such that the polymer may be a homopolymer or a heteropolymer. Representative polymers include peptides, polysaccharides, nucleic acids and the like, where the polymers may be naturally occurring or synthetic. The term "oligomer" is used herein to indicate a chemical entity that contains a plurality of monomers. As used herein, the terms "oligomer" and "polymer" are used interchangeably, as it is generally, although not necessarily, smaller "polymers" that are prepared using the functionalized substrates of the invention, particularly in conjunction with combinatorial chemistry techniques. Examples of oligomers and polymers include polydeoxyribonucleotides (DNA), polyribonucleotides (RNA), other polynucleotides which are C-glycosides of a purine or pyrimidine base, polypeptides (proteins), polysaccharides (starches, or polysugars), and other chemical entities that contain repeating units of like chemical structure. In the practice of the instant invention, oligomers will generally comprise about 2-50 monomers, such as about 2-20, and including about 3-10 monomers.

The term "nucleic acid" as used herein means a polymer composed of nucleotides, e.g., deoxyribonucleotides or ribonucleotides, or compounds produced synthetically (e.g., PNA as described in U.S. Pat. No. 5,948,902 and the references cited therein) which can hybridize with naturally occurring nucleic acids in a sequence specific manner analogous to that of two naturally occurring nucleic acids, e.g., can participate in Watson-Crick base pairing interactions.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "peptide" as used herein refers to any polymer compound produced by amide formation between an α-carboxyl group of one amino acid and an amino group of another group.

The term "oligopeptide" as used herein refers to peptides with fewer than about 10 to 20 residues, i.e., amino acid monomeric units.

The term "polypeptide" as used herein refers to peptides with more than 10 to 20 residues.

The term "protein" as used herein refers to polypeptides of specific sequence of more than about 50 residues.

The term "lipid matrix" as used herein means a molecular matrix containing natural, synthetic or combinations thereof of lipid molecules capable of forming a lyotropic phase (i.e., formation of an ordered structure upon interaction with water). The lipid molecules have intermediate molecular weight of about 100-5000 and contain a substantial portion of aliphatic or aromatic hydrocarbon. Includes one or more polar lipids such as phospholipids, lysophospholipids, sphingolipids, and glycolipids capable of forming lamellar bilayers and other lipid aggregates having various two-dimensional lamellae and/or hexagonal phase lattice structures and/or three-dimensional cubic phase lattice structures.

The term "oligonucleotide" as used herein denotes single-stranded nucleotide multimers of from about 10 up to about 200 nucleotides in length, e.g., from about 25 to about 200 nucleotides ("nt"), including from about 50 to about 175 nt, e.g. 150 nt in length The term "polynucleotide" as used herein refers to single- or double-stranded polymers composed of nucleotide monomers of generally greater than about 100 nucleotides in length.

DETAILED DESCRIPTION

Methods and compositions for synthesizing polymers, such as nucleic acids, are provided. Aspects of the invention include methods in which lipids and monomeric precursors, e.g., mononucleotides, of the desired product polymer are combined to produce a reaction mixture. The reaction mixture is then subjected to one or more steps of drying and rehydrating to produce a desired polymeric product, e.g., nucleic acid. Also provided are the polymeric, e.g., nucleic acid, products produced by the subject methods, as well as systems and kits for practicing embodiments of the invention.

Before the present invention is described in greater detail, it is to be understood that this invention is not limited to particular embodiments described, as such may vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely,"

"only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

Methods

Aspects of the invention include methods of synthesizing a polymer, e.g., a nucleic acid. Embodiments of the methods include combining a monomeric precursor, e.g., mononucleotide, composition and a lipid composition, e.g., present as fluid compositions, to produce a fluid reaction mixture. The resultant fluid reaction mixture is then dried to produce a dried reaction mixture, and then rehydrated to produce a product comprising a synthesized product polymer, e.g., nucleic acid, that has been synthesized, e.g., via a condensation reaction, from the mononucleotides present in the mononucleotide composition. In certain embodiments, the method comprises at least two iterations of the drying and rehydrating steps. While the present invention is broadly 5, applicable to non-enzymatic based synthesis of a variety of different types of polymers, for ease of description the invention is now reviewed in greater detail with respect to nucleic acid embodiments. However, the scope of the invention is not so limited.

In certain embodiments where the product polymer is a nucleic acid, the nucleic acid is a ribonucleic acid. In certain embodiments where the monomeric precursors are mononucleotides, the mononucleotide composition comprises ribonucleotides, e.g., adenosine 5'-monophosphate and uridine 5'-monophosphate. In certain embodiments, the product nucleic acid is a homopolymer while in other embodiments the product nucleic acid is a heteropolymer. In certain embodiments, the mononucleotide composition and the lipid composition are combined in manner sufficient to provide for a mononucleotide to lipid molar ratio in said reaction mixture that ranges from 2:1 to 1:2. In certain embodiments, the drying comprises subjecting the reaction mixture to a stream of dry gas, e.g., carbon dioxide. In certain embodiments, the rehydrating comprises contacting the dried reaction mixture with an aqueous fluid, e.g., an acidic fluid, such as 1 mM HCl. In certain embodiments, the method further comprises separating product nucleic acids from lipids. In certain embodiments, the nucleic acid ranges in length from about 10 to about 500 nt or longer, such as from about 20 to about 250 nt or longer, e.g., from about 40 nt to about 100 nt or longer. In certain embodiments, the product nucleic acid is linear. In certain embodiments, the method does not employ activated nucleotides.

A typical polymerization reaction involves exposing the mononucleotide and lipid composition to one or more cycles of wetting (hydration or rehydration) and drying (dehydration). Reaction conditions for a given cycle of wetting and drying are selected to maintain the desired interaction of the lipid matrix-embedded nucleotides. Parameters of particular interest include the ratio of lipid to nucleotide, pH and temperature, solvent content, composition of the lipid matrix, solubility of the nucleotides and ratio of nucleotide monomers. The conditions can be adjusted and optimized as illustrated in the working examples.

For example, the polymerization reaction can be carried out with about 1-20, 1-15 or 1-10, and usually about 1-7 cycles of wetting and drying. The cycle starts with admixing of the lipid and nucleic acid materials and any other excipients to produce the fluid reaction mixture. The molar ratio of mononucleotide to lipid is generally about 2:1, 1:1 or 1:2, and is readily dissolved in an aqueous fluid such as a protic acid solution. More specifically, the mononucleotide to lipid ratio generally includes fractional increments of 0.1, 0.2, 0.3, 0.4, 0.5, 0.6, 0.7, 0.8, 0.9 and 1.0 over a range of mononucleotide to lipid ratio of about 2:1, 1.9:1.1, 1.8:1.2, 1.7:1.3, 1.6:1.4, 1.5:1.5, 1.4:1.6, 1.3:1.7, 1.2:1.8, 1.1:1.9 and 1:2. The pH of the fluid reaction mixture can vary, but is usually in a pH range of around 2 to 9, and more typically around neutral to acidic pHs. This includes a pH of the reaction mixture with fractional increments of 0.1, 0.2, 0.3, 0.4, 0.5, 0.6, 0.7, 0.8, 0.9 and 1.0 over a pH range of about 2, 3, 4, 5, 6, 7, 8 and 9. The mixture may be buffered or un-buffered and include one or more additional excipients such as a salt, a detergent and the like.

Once the reactants are admixed, the drying cycle is initiated to generate the dried reaction mixture. Drying of the fluid reaction mixture concentrates the reaction materials within the lipid system so as to drive the condensation reaction and polymer elongation. As noted above, drying can be carried out by exposing the sample to a dry gas to accelerate drying of the fluid reaction mixture. The sample can be exposed to the dry gas for either a specific time or variable time interval, for instance, typically around 30-120 minutes depending on the reaction volume. The drying process can be further accelerated in conjunction with heating. The heating temperature generally ranges from about room temperature up to about 99° C., and on average from ambient temperature up to around 90° C.

Thus drying can be carried out by various approaches. Of specific interest are drying methods that reduce cycle times and aid in monomer activation and polymerization. Examples include a stream of gas, vacuum and the like. The gas can be a mixture of gases (e.g., air), or substantially a single type of gas (e.g., $CO_2$). Gases of interest include non-inert gases such as air and carbon dioxide, or inert gases such as nitrogen and argon, and the like, with carbon dioxide being of particular interest. As can be appreciated, flow rates for the stream of gas can be adjusted to optimize the process, as well as carried out under various atmospheric pressures.

Drying also may include subjecting the reaction mixture to a non-streaming gas or vacuum (e.g., lyophilization). In another embodiment, drying is accomplished by a combination of a stream of gas and lyophilization. Drying may also be carried out under variable temperature and/or pH. For instance, the fluid reaction mixture can be dried at a temperature that minimizes inhibition of polymerization or degradation of the lipid matrix and polymerization product, while maximizing the drying process. Temperature ranges for drying include below 0° C. to around 100° C. Temperature ranges of specific interest for drying generally include increments of 1, 2, 3, 4, 5, 6, 7, 8, 9 and 10 degrees over a range of about 0, 10, 20, 30, 40, 50, 60, 70, 80, 90 and 100° C.

While the dried reaction mixture can be immediately rehydrated, the dried reaction mixture may also be allowed to incubate for a period of time sufficient for polymerization of monomer. Reaction times are generally chosen so as to optimize polymerization. Exemplary incubation times for the dried reaction mixture are 5 minutes or longer and typically include increments of 0.1, 0.2, 0.3, 0.4, 0.5, 0.6, 0.7, 0.8, 0.9, 1, 2, 3, 4, 5, 6, 7, 8, 9 and 10 minutes of a range of about 10, 20, 30, 40, 50, 60, 70, 80, 90, 100, 110, 120, 130, 140, 150, 160, 170 or 180 minutes or longer (e.g., overnight, or even longer such as when placed in short or long term storage), and more typically 30 minutes to 120 minutes. The dried reaction mixture can be sampled and tested, stored for later use, or followed by a rehydration step during which the lipid matrix is re-solvated.

Rehydration of the dried reaction mixture generates a nucleic acid product that has been synthesized via a condensation reaction from the mononucleotides present in the mononucleotide composition. Rehydration generally takes between 5 and 30 minutes depending on reaction volume, gas exposure and heating. For example, rehydration takes on average about 10 minutes for a 0.5 ml reaction volume under a stream of carbon dioxide at around 90° C. The rehydration solvent can be the same solvent system employed in the first cycle, and is usually a weak aqueous protic acid solution with or without buffer.

The rehydrating process provides several features of the reaction conditions necessary for promoting polymerization. One feature facilitates contact of the reaction components and lipid matrix with an aqueous fluid. The aqueous fluid is typically selected to increase polymerization (e.g., phosphodiester bond formation) while reducing unwanted side reactions (e.g., phosphodiester bond hydrolysis, degradation of the lipid matrix etc.). Of specific interest are aqueous fluids in which formation of activated mononucleotide is promoted, such as a phosphoester in an acidic medium, as well as stability of the lipid matrix is promoted.

The acidic fluid can be formed from monoprotic (e.g., hydrochloric acid, nitric acid) or polyprotic acids (e.g., diprotic acids such as carbonic acid, sulfuric acid, and triprotic acids such as citric acid, phosphoric acid). This includes mineral acids such as hydrochloric and sulfuric acid, other common acids such as hydrobromic and chromic acid, as well as the sulphonic acids such as methane, ethane, benzene and toluene sulphonic acids.

Of specific interest are aqueous fluids having a pH and ionic concentration for optimizing the polymerization of mononucleotides in conjunction with the repeated drying and wetting steps of the subject methods. This includes, for example, acidic fluids with properties similar to an acidic fluid prepared with a protic acid such as HCL. In particular, acidic fluids with properties similar to an acidic fluid prepared with 0.1 to 100 mM HCL, 0.1 to 10 mM HCL, or 0.5 to 5 mM HCL, and more specifically about 1 mM HCL are of specific interest. It will be readily apparent that the pH and ionic concentration of the fluid can be adjusted for a given end use, provided that for polymerization the reactivity and integrity of the reactants and products are respectively maintained.

Following rehydration, the sample can be incubated in a manner similar to the drying cycle, and/or immediately exposed to further drying (dehydration) and wetting (rehydration) cycles. Thus the drying and rehydrating steps are performed until the desired material is generated. This is generally involves repeating the wetting and drying steps one or more times. For example, the polymerization reaction can be carried out with about 1-20, 1-19, 1-18, 1-17, 1-16, 1-15, 1-14, 1-13, 1-12, 1-11, 1-10, 1-9, 1-8, 1-7, 1-6, 1-5, 1-4, 1-3, 1-2 or a single cycle, and usually about 1-7 cycles of wetting and drying. As noted above, the drying and rehydration cycle generates polynucleotide in a condensation reaction that condenses, for example, the 5'-phosphate group of one nucleotide or chain with the 3'-hydroxyl group at the end of another nucleotide or chain.

The cycle parameters can be the same or different from cycle to cycle. Thus it is not necessary to repeat identical cycle parameters as the conditions and reaction variables can each individually be held constant, adjusted or allowed to change without intervention over the course of one or more subsequent cycles. For example, while the starting pH is typically neutral and the solvent system is a weak protic acid solution, the to pH can tend towards acidic if allowed to run multiple cycles without adjusting the pH. The pH is just one example, and of course other parameters can be held constant, adjusted or allowed to change over the course of one or more reaction cycles. This includes time, temperature, pH, ratio of lipid to nucleotide, solvent content, composition of the lipid matrix, ratio of nucleotide monomers and the like.

The resulting polynucleotide reaction product is thus produced by one or more repeated cycles of drying and rehydration. And depending on the nucleic acid materials and conditions employed in a given polymerization reaction, linkages between monomers of the polynucleotide chain can vary. For example, the subject methods can generate polynucleotide chains with 2'-5' and 3'-5' phosphodiester linkages for the standard mononucleotides as well as combinations thereof. The nucleotides may also be linked by one or more non-nucleotide components capable of adjoining two or more nucleotide monomers in the subject methods.

The resulting polynucleotide reaction product may also include polynucleotide chains of variable lengths and configurations. This includes dimers, trimers and longer, as well as single and double stranded chains, linear, branched, cyclic or combinations thereof. The polynucleotide chains can be up to 10 kilo base pairs (kb) or in some instances longer. Polynucleotide chains of particular interest are those having a nucleotide length of about 10 to about 5000 or greater, including various ranges therein in increments of 1, 2, 3, 4, 5, 6, 7, 8, 9 and 10 nucleotides over a range of chains in incremental lengths of 10, 20, 30, 40, 50, 60, 70, 80, 90 and 100 nucleotides in length. This includes specific chain lengths ranging from 2, 10, 50, 100, 500, 1000, 1500, 2000, 3000, 4000, 5000, 6000, 7000, 8000, 9000 and 10000 nucleotides as examples. Thus, one advantage of a non-enzymatic polymerization reaction employing a wet and dry phase is that the product chain lengths can be short or quite long relative to enzymatic polymerization products.

The subject method may optionally include the step of separating product nucleic acids from the lipid matrix. The separation can be carried out by various standard techniques (see, e.g., (Lindblom et al. *Biochimica et Biophysica Acta* (1989) 988:221-256), and typically involves dispersion in water followed by extraction in organic solvent (e.g., aqueous solution of n-butanol 2:1 by volume, followed by hexane to remove excess remaining butanol) and drying. Chromatographic separations also may be employed, such as affinity-based chromatography, size-based chromatography, charge-based chromatography, and/or combinations thereof and the like (e.g., high performance liquid chromatography (HPLC), ion exchange, gel permeation or size exclusion, gel electrophoresis etc.). Removal of other excipients when present can be carried out as well, for example, removal of detergent and/or salt etc. by dialysis, and the like. Assessment of the purity, quantity and quality of the nucleic acid material can be carried out as described in the Examples, and variety of other standard techniques for nucleic acid analysis.

As also noted above, mononucleotides suitable for or that benefit from use of the subject methods include, but are not limited to, the standard ribonucleotides and deoxyribonucleotides, as well as derivatives thereof. The mononucleotides bear one or more groups capable of forming a covalent linkage between one or more other mononucleotides in the reaction mixture. This includes derivatives of the standard nucleobases (often referred to simply as bases) cytosine, guanine, adenine, thymine and uracil (abbreviated as C, G, A, T, U, respectively), as well as derivatives such as hypoxanthine and xanthine, and derivatives of the ribose and deoxyribose sugar rings. For instance, mononucleotides suitable for use in the subject methods can bear a phosphate group and a hydroxyl group. Of particular interest is a first mononucleotide having a phosphate group that is capable of forming a phosphodiester bond with a second mononucleotide bearing a mutually reactive hydroxyl group. Formation of the phosphodiester bond is driven in situ by lipid-mediated conversion of the phosphate to a reactive ester in conjunction with the drying and rehydration cycles. Monomers bearing both a reactive phosphate and hydroxyl facilitate polymerization, where reaction of the phosphoester and hydroxyl generate a polynucleotide chain having one or more monomers linked through one or more phosphodiester bonds. Thus while pre-activated mononucleotides can be employed, the subject method does not require use of pre-activated nucleotides for polymerization.

The nucleic acid can be a homopolymer or a heteropolymer depending on the mononucleotides employed in a given polymerization reaction. Homopolymers are produced from incorporation of the same mononucleotides, such as a reaction mixture containing the same ribonucleotides or deoxyribonucleotides. Heteropolymers are produced by incorporation of different mononucleotides into a polymer chain, such as a mixture of two or more different ribonucleotides or deoxyribonucleotides. Examples of specific mononucleotides of interest include adenosine 5'-monophosphate, guanidine 5'-monophosphate, cytidine 5'-monophosphate, thymidine 5'-monophosphate and uridine 5'-monophosphate, as well as derivatives such as capped and labeled versions (see, e.g., those described in *Oligonucleotides and Analogues, A Practical Approach*, F. Eckstein, editor, IRL Press, Oxford, 1991).

Mononucleotide derivatives of particular interest include those that contain various modifications at single or multiple positions of the nucleotide moiety (see, e.g., U.S. Pat. No. 5,547,835 and International PCT application No. WO 94/21822). The modifications can be wide ranging (see, e.g., Nakamaye et al. *Nucl. Acids Res.* (1988) 16:9947 59; Porter et al. *Biochemistry* (1995) 34:11963 11969; Hasan et al. *Nucleic Acids Res.* (1996) 24:2150 2157; Li et al. *Nucl. Acids Res.* (1995) 23:4495 4501). By way of example, the moiety can be attached either to the nucleobase, to the phosphate group at the alpha phosphate of the nucleoside or nucleotide, or at the 2'-position or 3' position of the sugar ring.

In a specific embodiment, nucleotide derivatives of particular interest include those modified to contain a detectable label, such as a radioactive hydrogen, phosphate or sulfur atom and the like, photoactive groups, as well as chromophores including fluorophores and other dyes, or a hapten such as biotin. Modified nucleotides comprising a detectable label and synthesis techniques used to make them are well known, and can be used for this purpose. For example, it may be convenient to conjugate a fluorophore to a suitable group using protecting group strategies.

Thus a detectable label can be attached to portion of the sugar or base of a resin-bound nucleotide before removal of other protecting groups and release of the labeled nucleotide from the resin. Fluorescein, eosin, Oregon Green, Rhodamine Green, Rhodol Green, tetramethylrhodamine, Rhodamine Red, Texas Red, coumarin and NBD fluorophores, the dabcyl chromophore and biotin are all reasonably stable to acidic conditions and thus suitable for incorporation via solid phase synthesis employing protecting acidic conditions. (Peled et al. *Biochemistry* (1994) 33:7211; Ben-Efraim et to al. *Biochemistry* (1994) 33:6966). Other than the coumarins, these fluorophores also are stable to reagents used for deprotection under stong basic conditions (Strahilevitz et al. *Biochemistry* (1994) 33:10951). The dabcyl chromophore can also be used as it has broad visible absorption and can used as a quenching group. EDANS is a common fluorophore for pairing with the dabcyl quencher in FRET experiments. Dansyl fluorophore is another label that, as with EDANS, has a fluorescence profile that overlaps the absorption of dabcyl. Site-specific biotinylation can also be employed. It will be recognized that other protected nucleotides for automated synthesis can be prepared by custom synthesis following standard techniques in the art.

Lipids of interest are those capable of forming amphiphilic structures. Amphiphilic (amphipathic) lipids have a hydrophilic (polar) head and a hydrophobic (non-polar) tail. In aqueous environments, the polar head groups face toward the water while their hydrophobic tail groups interact with each other to create a lamellar bilayer, and to a lesser extent other aggregate structures depending on the lipid composition and conditions. For example, amphiphilic lipids can form a variety of different shapes including spheres (vesicles), rods (tubes) and lamellae (plates) depending on lipid and water content, and temperature. These shapes represent basic units that interact to form two- and three-dimensional lattice matrix structures classified as lamellar phase (e.g., bilayer plate, closed sphere), hexagonal phase (e.g., rod), or cubic phase (e.g., spheres, rods or lamellae connected by solvent channels) (Lindblom et al., supra). A cross section of a typical lipid bilayer (lamellar phase) in water can be viewed as having a hydrophobic core region of about 30 Angstroms with two interfacial regions of about 15 each (White et al. *Curr. Struc. Biol.* (1994) 4:79-86).

Of specific interest are lipid compositions that form a structured microenvironment under the drying and rehydration cycles of the subject methods suitable for organizing nucleotide monomers into one-dimensional and/or two-dimensional arrays while permitting their diffusional mobility. One- and/or two-dimensional organization of the monomers facilitate alignment of reactive groups. Diffusional mobility increases contact frequency and duration of reactive groups so as to allow them to undergo condensation reactions. To this end, amphiphilic lipids can form one or more layers of lamellar films capable of trapping solute between the lamellae of the lipid films when admixed with solute. In this way the lamellar microenvironments impose order on mononucleotides in such a way that they are able to form phosphodiester bonds to produce one or more polynucleotide strands of interest.

The lipid matrix into which the nucleotide component is incorporated includes natural and synthetic lipids capable of forming a lyotropic phase (i.e., formation of an ordered membrane type structure on interaction with water, such as a liquid crystalline phase). These include polar lipids such as phospholipids, lysophospholipids, sphingolipids, and glycolipids capable of forming lamellar bilayers and other lipid aggregates. Particular lipid matrices of interest form stable membrane monolayers or bilayers and aggregate phases thereof. This includes lipids that form stable cubic phases (cubic lipidic phase or CLP matrix) (Luzatti, et al., Nature (1968) 218:1031-1034; and Lindblom, et al., Biochimica et Biophysica Acta (1989) 988:221-256). A cubic phase is one in which the lipid aggregates form a three-dimensional lattice. The lipid aggregate units can have different shapes such as spheres, rods, or lamellae. In contrast, lamellar liquid crystalline phases exhibit a one-dimensional periodicity in which lamellar units of infinite expression are stacked regularly, and hexagonal liquid crystalline phases exhibit a two-dimensional periodicity with rod-like aggregates of infinite length packed into a hexagonal lattice. Thus, cubic phases are optically isotropic whereas lamellar and hexagonal phases are optically anisotropic.

Lipids that form cubic phases consist of multiple lipid bilayers protruded by multiple solvent channels formed between certain lipids and polar solvents at specific lipid:solvent ratios (Luzatti et al., supra; and Lindblom et al., supra). The lipid diffusion rate inside the CLP is comparable to the rate in lamellar lipid phases and that the diffusion rate in the aqueous compartments is approximately three times slower than in bulk water (Lindblom et al., supra). Additionally, biological molecules can exhibit full activity when incorporated into cubic phase lipids (Portmann et al. *J. Phys. Chem.* (1991) 95:8437-8440). Since CLPs are optically isotropic, they can be employed in sensitive spectrophotometric assays. Thus, manipulation of nucleotides incorporated into a lipid matrix not only provides a unique system for polymerization of monomers, the lipid matrix itself can be exploited to facilitate assays that require lipid-mediated polymerization.

The lipid matrix component may include natural and/or synthetic lipids capable of forming a lyotropic phase (e.g., liquid crystalline phase upon interaction with water). Of particular interest are polar lipids such as phospholipids, lysophospholipids, sphingolipids, and glycolipids capable of forming lamellar bilayers and other lipid aggregates, which includes mixtures of lipids capable of forming a lyotropic crystalline phase. Examples of such lipids include, but are not limited to, insoluble non-swelling amphiphiles, insoluble swelling amphiphiles, and various soluble amphiphiles capable of forming lyotropic liquid crystalline phases. Examples of insoluble non-swelling amphiphiles include triglycerides, diglycerides, long chain protonated fatty acids, long chain normal alcohols, long chain normal amines, long chain aldehydes, phytols, retinols, vitamin A, vitamin K, vitamin E, cholesterol, desmosterol, sitosterol, vitamin D, unionized phosphatidic acid, sterol esters of very, short chain acids, waxes in which either acid or alcohol moiety is less than 4 carbon atoms long (e.g., methyl oleate), and ceremides. Examples of insoluble swelling amphiphiles include phosphatidylcholine, phosphatidylethanolamine, phosphatidylinositol, sphingomyelin, cardiolipin, plasmalogens, ionized phosphatidic acid, cerebrosides, phosphatidylserine, monoglycerides, acid-soaps, .alpha.-hydroxy fatty acids, monoethers of glycerol, mixtures of phospholipids and glycolipids extracted from cell membranes or cellular organelles (plant glycolipids and sulfolipids), sulfocerebrosides, sphingosine (basic form). Examples of soluble amphiphiles capable of forming lyotropic liquid crystalline phases include sodium and potassium salts of long chain fatty acids, many of the ordinary anionic, cationic, and nonionic detergents, lysolecithin, palmitoyl and oleyl coenzyme A, and other long chain thioesters of coenzyme A, gangliosides, and sphingosine (acid form).

Examples of suitable amphiphilic lipids that form stable monolayers or bilayers and aggregate phases thereof include, but are not limited to, the following lipids: phosphatidylcholine (PC); dipalmitoylphosphatidylcholine (DPPC); 1-palmitoyl-2-oleoylphosphatidylcholine (POPC); palmitoyl-oleoylphosphatidic acid (POPA); dioleoylphosphatidylcholine (DOPC); dilinoleoylphosphatidylcholine (DIiPC); lysophosphatidylcholine (LPC); 1, palmityol-LPC (PaLPC); 1-oleoyl-LPC (OILPC); 1, monoolein (MO); phosphatidylethanolamine (PE); plasmaenylethanolamine (PalE); glycerol acetal of plasmaenylethanolamine (GAPIaE); didodecylphosphatidylethanolamine (DDPE); dielaidoylphosphatidylethanolamine (DEPE); dioleoylphosphatidylethanolamine (DOPE); dilineoleoylphosphatidylethanolamine (DIiPE); dioleoylphosphatidyl-N-monomethyl-ethylethanolamine (DOPE-Me); diphosphatidylglycerol (DPG); phosphatidylglycerol (PG); phosphatidylserine (PS); phosphatidylinositol (PI); monoglucolsyldiacylglycerol (MgIuDG); monogalactosyldiacylglycerol (MgaIDG); diglucosyldiacylglycerol (DgluDG); digalactosyl-diactylglycerol (DgalDG); dioleoyl-monoglucosyldiacylglycerol (DOMGIuDG); dioleoyldiglucosyldiacylglycerol (DODGIuDG); glyceroldialkylnonitol tetraether (GDNT); and a glycerol-lipid mixture of 70% of GDNT with .beta.-D-glycopyranose linked to the nonitol group; 30% of glycerol dialkyl glycerol tetraether with .beta.-D-galactopyranosyl-.beta.-D-galactopyranose linked to one of the glycerol groups (GL). Those of specific interest are POPC, POPA and LPC.

The lipids may be obtained from various sources including commercial sources or produced and prepared as micelles, liposome vesicles, CLP matrices, or continuous lamellar membranes purified from cells following standard techniques known in the art. (See, e.g., Small D M, (1986) "*The physical chemistry of lipids from alkenes to phospholipids,*" In: *Handbook of Lipid Research*, vol. 4, pp. 1-672, D. Haccham, ed,. Plenum Press New York; Winterhalter et al., *Chem. Phys. Lipids* (1993) 64(1-3):35-43; McNamee, M G., *Biotechniques* (1989) 7(5): 466-475; Albertsson et al., *Methods Biochem Anal.* (1982) 28: 115-150; Graham J M., Methods Mol. Biol. (1993) 19: 97-108; and Kinne-Saffran et al., *Methods Enzymol.* (1989) 172: 3-17; Larsson K., *J. Phys. Chem.* (1989) 93:7304-7314; Zumbuchl et al., *Biochimica et Biophysica Acta* (198×) 640:252-262; Erikson et al., *J. Phys. Chem.* (1985) 91:846; Seddon et al., *Prog. Colloid Polym. Sci.* (1990) 81:189; and U.S. Pat. No. 5,554,650).

The lipid matrix can be chosen for optimal compatibility with the nucleotide reagents as well as the drying and rehydration steps. In this instance nucleotides or polynucleotides known to be stable over a particular temperature range are selected for to incorporation in a lipid matrix having a compatible temperature profile. The temperature profile for formation of the desired lipid matrix and corresponding microenvironment can also be chosen so as to be compatible with incorporation and stability of the mononucleotide of interest. For instance, a rehydrated lipid matrix comprising a MO/water solvent system is stable at room temperature (about 25° C.). Thermostable lipid systems on the other hand may be more suited for applications involving elevated temperatures. For example, a rehydrated lipid matrix comprising a DOPE/water system having a temperature minimum profile for formation of the cubic phase of about 70° C.

More specifically, the solvent content, temperature and lipid composition employed in the rehydration process can be varied to modulate the reaction conditions. For example, lipid systems that include mixtures of MO with 1-palmitoyl-2-oleoyl-3-phosphatidylserine (PaOIPS) and DEPE/alamethicin form bicontinuous cubic phases under fully hydrated conditions within certain concentration ratios and temperature ranges. In contrast, DOPE with up to 10 mol % PaOIPS exists in the hexagonal phase at room temperature. Thus temperature and composition of the lipid membrane can be used to control the crystalline phase. Such parameters are known for many lipid systems, or can be determined by various methods known in the art, including testing a serial array of mixtures with various concentrations of particular lipid components and solvent, and comparing them over a range of temperatures. More specialized techniques also can be employed to fine tune the cubic phases of a particular lipid/solvent system, such as determination of phase diagrams, X-ray diffraction, NMR, and polarized light microscopy and the like (Lindblom, et al., supra).

This includes lipid systems chosen to form various specific structures based on solvent content by weight percent (wt %) and minimum temperature (° C.) of formation. For instance, several lipid systems form a cubic lipidic phase structure under specific solvent and temperature conditions. These include, but are not limited to: MO with 12-40 wt % water content and temperature minimum of 20° C.; PaLPC with 40-46 wt % water content and temperature minimum of 25° C.; OlLPC with 20-25 wt % water content and temperature minimum of 25° C.; Egg PC with 0-4 wt % water content and temperature minimum of 75° C.; DOPC with 2-11 wt % water content and temperature minimum of 60° C.; DIiPC with 4 wt % water content and temperature minimum of 55° C.; Egg PC+22-35 wt % sodium cholate with 22-26 wt % water content and temperature minimum of 22° C.; Egg PC+75-80 wt % diacylglycerol with excess water content and temperature minimum of 10° C.; Egg PC+85 wt % DIiPE with excess water content and temperature minimum of 40° C.; DOPE with 67 wt % water content and temperature minimum of 25° C.; DOPE-Me with 67 wt % water content and temperature minimum of 25° C.; DOPC+0-50 wt % DOPE with water content of 10 wt % and temperature minimum of 70° C.; POPC+85-90 wt % DIiPE with 29-41 wt % water content and temperature minimum of 7° C.; PE from *P. regina* with water content of 35-50 wt % and temperature minimum of 40° C.; PE from *B. megaterium* with 8-26 wt % water content and temperature minimum of 58° C.; DDPE with water content of 10-16 wt % or greater than 33 wt % and temperature minimum of 75° C. or 115° C., respectively; DPG from bovine heart+29 wt % dibucane with 41 wt % water content and temperature minimum of 7° C.; sodium sulfatide from human brain with 40-70% water content and temperature minimum of 20° C.; DOMGIuDG from *A. laidlawii* with 7-15 wt % water content and temperature minimum of 0° C.; DOMGIuDG+51 wt % DODGIuDG from *A. laidlawii* with 10 wt % water content and temperature minimum of 25° C.; MgaIDG+31 wt % DgaIDG from maize chloroplasts with 10-20 wt % water content and temperature minimum of 60° C.; MgaIDG 34-50 wt %+DgaIDG from wheat chloroplasts with water content of 3-15 wt % and temperature minimum of 10° C.; GDNT with 7-13 wt % water content and temperature minimum of 15° C.; GL with 0-11 wt % water content and temperature minimum of 60° C.; polar lipids from *A. laidlawii* with 18 wt % water content and temperature minimum of 65° C.; and polar lipids from *S. solfactaricus* with water content of 20 or 40 wt % and temperature minimum of 85° C. (Lindblom, et al., supra).

Addition or exclusion of one or more reagents that solubilize the lipid matrix and/or the nucleotide mixture to different extents may further be used to control the specificity and rate of the desired polymerization reaction, i.e., control exposure and presentation of reactive groups by manipulating solubility of the lipid matrix and/or nucleotide mixture. Reaction conditions are readily-determined by assaying for the desired reaction product compared to one or more internal and/or external controls. One or more excipients can be added to the reaction mixture to aid the drying process. This includes the optional addition of one or more solvents such as an organic solvent. Organic solvents of particular interest are those that maintain or facilitate the desired lipid composition and structure. Examples of organic solvents include, but are not limited to, methanol, ethanol, propanol, butanol, hexane and the like. In general, however, the acidic aqueous solution typically constitutes the bulk solvent, and organic solvents if employed are present in disproportionate amounts.

Also, a given nucleotide mixture of interest can be reconstituted in a preformed lipid matrix by controlled solubilization and/or lipid extraction techniques. For instance, the nucleotides can be added to an appropriate solvent/detergent system, and extracts admixed with a preformed lipid matrix that contains or is devoid of solvent/detergent in an amount that permits solubilization and insertion of the nucleic acid materials into the lipid matrix. As noted above, one or more reconstitution conditions may be adjusted to optimize the process, such as temperature, pH, water and/or organic solvent content, ion concentration, reducing or oxidizing reagents if present, as well as ratios of detergent to lipid, detergent to nucleotide, and lipid to nucleotide. An example is admixing a lipid matrix and nucleotide in an appropriate buffer system with serial amounts of a detergent, and monitoring nucleotide incorporation at each step of the reconstitution process to assess optimal buffer/detergent profiles for a particular lipid-nucleotide reconstitution system. Examples of lipid solubilization reagents suitable for reconstitution and analyses include SDS (sodium dodecyl sulfate), Triton-X100, Ammonyx-LO (N,N-dimethyl lauryl amine oxide), sodium cholate, taurocholate, sucrose monolaurate, dodecylmaltoside, CHAPS (3-(3-cholamidopropyl)-dimethylammonio-1-propanesulfonate), CHAPSO (3-[(3-cholamidopropyl)dimethylammonio]-2-hydroxy-1-propane sulfonate), octylglucoside, octylgiucopyranoside and the like. (See, e.g., Rigaud et al., *Biochimica et Biophysica Acta* (1995) 1231(3): 223-246; Yang et al., *Anal. Biochem.* (1994) 218(1):210-221; Scotto et al, *Biochemistry* (1987) 26(3):833-839). If necessary, detergent can be removed following reconstitution and the content and/or activity of the reconstituted system characterized by various methods known in the art.

Reconstitution by lipid extraction can be performed through addition of nucleotide to a lipid matrix in an appropriate organic solvent system, such as a hexane and buffered aqueous solution, for separation of aqueous soluble phase from lipid-organic solvent soluble phase. As with the solvent/detergent solubilization method above, one or more reconstitution conditions may be adjusted to optimize the process, such as temperature, pH, water and/or organic solvent content, ion concentration, reducing or oxidizing reagents if present, as well as ratios of detergent to lipid, detergent to nucleotide, and lipid to nucleotide. The extracted lipid phase containing the nucleotide can then be employed to form lipid monolayers, bilayers, liposome, micelles or CLPs by standard techniques such as sonication, layering, extrusion, centrifugation and the like depending on the lipid matrix to be obtained. Any suitable technique for reconstitution of nucleotides in a lipid matrix by lipid extraction can be used. (See., e.g., Montal, et al., Q. Rev. Biophys. (1981) 14:1-79; Ayala, et al., Biochimica et Biophysica Acta (1985) 810(2):115-122; Montal, et al., Proc. Natl. Acad. Sci. USA (1990) 87:6929; Puu, et al., Biosen Bioelectron (1995) 10(5):463-476). For instance, the solvent system can be selected for a particular lipid-nucleotide mixture to optimize extraction, such as described above for obtention and preparation of lipids. As with the solubilization method of incorporating nucleotides in a lipid matrix, serial amounts of a chosen solvent with or without detergent and/or salts can be employed to monitor and select an optimal lipid extraction system to obtain an extracted lipid phase containing the nucleotide monomers.

As is apparent, the subject methods can be use to generate, isolate and/or amplify a fragment of RNA or DNA by polymerization of individual monomers, polynucleotide fragments, and/or combinations thereof. For instance, the subject methods also may employ one or more polynucleotide templates that contain a region of the polynucleotide fragment to be synthesized. This includes use of one or more primers as a polymerization catalyst and/or as elongation template. The primers are complementary to the nucleotide regions of interest, including complementation at the 5' and 3' ends as well as sequences internal to the 5' and 3' ends of the target region to be synthesized (or amplified). In this embodiment, one or more of the dehydration and rehydration cycles can include an initialization step of denaturation, annealing, or both denaturation and annealing. The denaturing step involves heating of the reaction mixture so as to ensure that most of the nucleic acid material is denatured and distributed proportionately in the lipid matrix with the other reactants. The initialization step also may include an annealing step in which the reaction temperature is lowered for a short period of time to allow annealing between primer, template and mononucleotides, depending on the melting temperature of the primers and the like. The initialization step is integrated with dehydration and rehydration cycling and repeated one or more times for polymerization.

The subject methods also may employ a combination of non-enzymatic and enzymatic synthesis. For instance, various enzymes can be used to manipulate the polynucleotide reaction products, such as when it is desired to modify s terminal end, perform restriction digest, ligations, enzymatic-based amplifications and the like. The methods can be performed without restrictions on the form of nucleic acid and it can be extensively modified to perform a wide array of genetic manipulations ranging from sequencing and the detection of genetic diseases, cloning, genetic fingerprinting and paternity testing, amplification and quantification in general including analysis, detection and sequencing among other applications such as quantification and comparison of gene expression. This includes various applications described in US patents such as: U.S. Pat. Nos. 5,948,902; 5,547,835; 6,599,284; 6,607,878; 6,632,645; 6,635,463; 6,673,616; 6,677,146; 6,692,917; 6,696,250; 6,699,979; 6,706,471; 6,706,474; 6,709,815; 6,753,169; 6,759,226; 6,762,022; 6,767,703; 6,780,982; 6,783,940; 6,825,009; 6,852,487; 6,870,026; 6,872,816; 6,875,572; 6,890,719; 6,893,819; 6,913,881; 6,992,180; 7,045,289; 7,045,319; 7,060,436; 7,060,440; 7,063,945; 7,067,643; 7,078,499; 7,083,917; 7,087,381; 7,101,672; 7,118,860; 7,135,312; 7,141,377; 7,150,982; 7,166,688; 7,183,052; 7,189,508; 7,192,708; 7,195,871; 7,198,893; 7,211,654; 7,214,522; 7,226,738; and 7,238,795.

It will also be apparent that the subject invention has many advantages and applications beyond nucleic acid synthesis. First, the amphiphilic structure can serve as a dry reaction medium to promote the assembly of a broad range of monomers into polymers. The synthesis of RNA from mononucleotides as illustrated in the experimental section is a specific example and not limiting of the broader concept. One reason the amphiphilic structures are unique in this regard is that they force the monomers into two-dimensional or even one-dimensional arrays, thereby promoting a reaction that cannot occur in bulk phase solution. They also concentrate the monomer in an anhydrous medium that remains fluid and thereby permitting diffusional mobility of the reactants that might otherwise be impossible in other dried states. Second, drying and rehydration cycles help bring monomers into contact as well as provide energy input to aid in driving the polymerization reaction. And third, use of amphiphilic structures in combination with drying and rehydration cycles generates a solid state system capable of polymerization of monomers in general as well as fragments and mixtures of monomers and fragments.

Systems

Aspects of the invention also include systems for producing nucleic acids. Embodiments of these systems may include lipids, e.g., present as a lipid composition; mononucleotides, e.g., present as a mononucleotide composition; a source of dry gas; and a rehydrating fluid, e.g., an acidic rehydrating fluid.

Systems of interest may further include a device for carrying out the subject methods. Examples are devices suitable for the automated polymerization (drying and rehydrating cycles) of mononucleotides in accordance with the subject methods. This device includes a first vessel for receiving and/or admixing nucleotides, lipid, solvent and the like. The first vessel is in fluid contact with a second vessel containing rehydrating solvent, and a third vessel containing a gas. The device may also include one or more additional vessels for holding and introducing a reaction ingredient as desired (e.g., lipid, nucleotides etc.), and thus may be in fluid contact with the first vessel. As can be appreciated, by "fluid contact" is intended to include plumbing systems as well as direct or indirect delivery systems such an automated dispensing system and the like.

The first vessel, and optionally the second and third vessel, is in thermal contact with a temperature regulator such that the temperature of each polymerization cycle and/or reaction ingredient can be controlled. The polymerization device or system may further include a master system and interface for programming and/or controlling the polymerization cycles, including ramp rates, reaction times, temperature, rehydration and solvent flow, admixing conditions, sampling and the like (such as with modern Polymerase Chain Reaction "PCR" Thermocyclers). The device may thus include solid state and/or computer components to aid in the operation of the system. The system may be attached to one or more other systems for manipulation and/or characterization of materials employed in and/or generated by the subject methods.

Kits

Aspects of the invention also includes kits of reagents that find use in practicing various embodiments of the methods. In certain embodiments, the kits include lipids and mononucleotides. The kits may further include additional components, e.g., a source of dry gas, a source of rehydrating fluid or precursor thereof, etc.

The various components of the kit may be present in separate containers or certain compatible components may be pre-combined into a single container, as desired.

In addition to the above components, the subject kits may further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information printed, in the packaging of the kit, in a package insert, etc. Yet another means would be a computer readable medium, e.g., diskette, CD, etc., on which the information has been recorded. Yet another means that may be present is a website address which may be used via the Internet to access the information at a removed site. Any convenient means may be present in the kits.

The following examples are offered by way of illustration and not by way of limitation.

EXPERIMENTAL

The materials and methods are described in Examples I-VI, followed by various results and related discussion in Examples VII-XI.

Example I

Reagents

Mononucleotides (adenosine 5'-monophosphate and uridine 5'-monophosphate), polyadenylic acid and polyuridylic acid were purchased from Sigma Aldrich. The lipids, POPC (palmitoyl-oleoylphosphatidylcholine), POPA (palmitoyl-oleoylphosphatidic acid) and LPC (lysophosphatidylcholine) were purchased from Avanti Polar Lipids Inc. All is other reagents were of Analytical grade from Fisher and Sigma-Aldrich.

Example II

Preparation of Lipid dispersions

The phospholipids concentrations used for the experiments were in the range of 10 mg/ml (POPA, POPC) to 15 mg/ml (LPC). POPA and LPC were procured as dry powders, so stock solutions were made directly by weighing required quantities and dispersing them in water. POPC was in chloroform, and the chloroform was first evaporated by a gentle stream of air. The lipid film was re-dissolved in an equal volume of ethanol. To prepare lipid vesicles, the ethanol solution was injected into the desired solution of mononucleotides to form small unilamellar vesicles (Stanley, W. M. Meth. Enzymol. 12, 404 (1968)).

Example III

Reaction Conditions

Mononucleotides and lipids were mixed in fixed mole ratios ranging from 2:1 to 1:2 and put through a series of hydration-dehydration cycles to simulate a fluctuating environment on the prebiotic Earth. In a typical reaction the reactants were exposed to 1-7 cycles of wetting and drying in a volume of 0.5 ml. A stream of carbon dioxide was used to dry the samples while they were exposed varying-temperature ranges and time intervals. The experimental variables were temperature (room temperature up to 90° C.), time (30-120 minutes), lipid composition and mole ratio of mononucletoide to lipid (2:1, 1:1 and 1:2). After each drying cycle the samples were re-dissolved in 1 mM HCl and allowed to rehydrate for 10 minutes, then exposed to a further dehydration cycle. The starting pH was 7.0, and this decreased to 2.2 at the end of 7 cycles.

When the cycle series was complete, the samples were dispersed in water, and the lipids were extracted twice with n-butanol (2:1 by volume) followed by hexane to remove excess remaining butanol. Some of the untreated samples were set aside for examination by light microscopy.

Example IV

Gel Electrophoresis: $^{32}$P-Labeling and Analysis of Reaction Products

The samples were ethanol-precipitated, and dissolved in 44 µl of water. For dephosphorylation, 1 µl of calf intestinal alkaline phosphatase (CIAP, 1 U/µl MBI Fermentas) was added along with 5 µl of 10xCIAP buffer, and the reaction was incubated at 37° C. for 30 min, followed by phenol extraction and ethanol precipitation. Glycogen (1 µl of—specify concentration) was added to facilitate precipitation of small amounts of RNA. The RNA aggregates were pelleted by centrifugation, then dissolved in 16 µl of water and labeled at the 5'-termini with $^{32}$P. Phosphorylation was carried out by adding 1 µl of T4 polynucleotide kinase (T4 PNK, 10 U/µl, New England Biolabs), 2 µl of 10×PNK buffer and 1 µl γ-[$^{32}$P]ATP, followed by incubation at 37° C. for 15 min. The end-labeled RNA-like polymers were purified by G50 spin columns (Amersham Biosciences) and stored at −20° C. For gel electrophoresis, 10 µl aliquots of the RNA samples were mixed with 3× denaturing loading solution (7 M urea, 10 mM EDTA, and 0.02% xylene cyanol and bromphenol blue) and separated by electrophoresis on 15% polyacrylamide gels containing 7 M urea, along with MW markers. $^{32}$P-labeled reaction products were quantified using a Molecular Imager FX and Quantity One-4.2.0 software (Bio-Rad).

Reaction yields were obtained by performing RiboGreen assays. The assay kit was obtained from BioTek Instruments, Inc., Winooski, Vt. The RiboGreen RNA quantitation assay is a very sensitive technique that can detect as little as 1 ng/mL RNA. A standard curve was first obtained for polyadenylic acid and this was in turn used to estimate the yields obtained in the experimental samples. Enzymatic hydrolysis was carried out with RNase 1 (Sigma).

Example V

Light Microscopy

Samples of the reaction mixture (15 µl) were stained with 0.1 mM ethidium bromide and examined by phase and fluorescence microscopy at 400× magnification.

Example VI

Nanopore Analysis

A nanopore instrument was used for single molecule analysis of RNA samples. The detailed method is described in Akeson et al. (Akeson, M., D. Branton, J. J. Kasianowicz, E. Brandin, and D. W. Deamer. Biophys. J. 77, 3227 (1999).). Briefly, in the nanopore instrument a U-shaped patch tube with a 30 micrometer diameter aperture is supported by a custom-made Teflon structure which contains two 90 µl wells connected through the patch tube. The wells were filled with 70 µl 1.0 M KCl-HEPES buffer, and a solution of diphytanoyl-sn-glycero-3-phosphocholine in hexadecane (25 mg/ml) was painted across the aperture to form a bilayer. Aliquots of alpha-hemolysin (10 µg/ml) were added to the cis side of the bilayer by pipetting and thoroughly mixed. Typically in 10-20 minutes a heptameric channel of hemolysin assembled and inserted into the bilayer, as detected by a steady 120 pA current at 120 mV applied potential. Samples to be analyzed were reconstituted in 14 µl of 1.0 M KCl/50 mM HEPES buffer, and applied to the cis side of the nanopore. When a linear polyanion such as single stranded RNA is captured by the electrical field in the pore, it is translocated through the pore by single molecule electrophoresis and its presence in the pore transiently blocks the ionic current. Translocation events were detected by an Axopatch 200B patch clamp amplifier and recorded using P-clamp 9.0 software. (Axon Instruments). Duration and amplitude were analyzed and plotted with Clampex and Clampfit software.

Example VII

Nanopore Detection of Individual RNA Molecules

We reasoned that if RNA polymers sufficiently long to have catalytic activity were synthesized from mononucleotides, yields were likely to be low. We therefore used a nanopore instrument to analyze solutions in which polymerization may have taken place. Nanopore analysis can detect single linear polyanions such as RNA and DNA (Kasianowicz, J., E. Brandin, D. Branton and D. W. Deamer. Proc. Natl. Acad. Sci. USA 93,13770 (1996); Akeson, M., D. Branton, J. J. Kasianowicz, E. Brandin, and D. W. Deamer. Biophys. J. 77, 3227 (1999); Howorka; S., Cheley, S., and Bayley, H. Nat Biotechnol. 19, 636 (2001); Meller A, Branton D. Electrophoresis. 23, 2583 (2002); and to Deamer, D. W. and D. Branton, Accounts Chem, Res, 35, 817 (2002)), and thus provides a highly sensitive method to scan solutions for products of a polymerization reaction. A commonly used nanopore is α-hemolysin, which self-assembles in a lipid bilayer into a heptamer containing a limiting aperture of 1.5 nm. In a typical application, a phospholipid bilayer is formed across a 20 µm aperture in a Teflon support that separates a cis and trans compartment containing 1.0 M KCl. A single α-hemolysin heptamer is permitted to insert into the bilayer. When a voltage of 120 mV is applied across the bilayer, an ionic current of 120 pA if driven through the pore. The nucleic acid sample is then added to the cis compartment, and the electric field produced in the pore captures single-stranded nucleic acids which are translocated through the pore by electrophoresis. Each translocation event is detected as a characteristic blockade of the ionic current. The amplitude and duration of the blockade provide information about the composition and length of the nucleic acid strand (see Deamer, D. W. and D. Branton, Accounts Chem, Res, 35, 817 (2002).).

Phospholipids (prepared as liposome dispersions in aqueous solutions) were mixed with mononucleotides at mole ratios of 2:1, 1:1 and 1:2. When phosphatidylcholine was used, lipid was injected as an ethanol solution into the aqueous phase to produce small unilamellar vesicles (Batzri, S., and Korn E. D. Biochim. Biophys Acta. 298, 1015 (1973)). Phosphatidic acid and lysophosphatidylcholine were dispersed by 1 min agitation in a vortex stirrer. The lipid concentration was typically 10 mg/ml, and additions of AMP, UMP or 1:1 AMP:UMP mixtures (as 5' mononucleoside phosphates) were adjusted to the desired mole ratio. Aliquots (0.5 ml) of the mixture were placed in glass test tubes in a standard heating block with the temperature adjusted to 60, 70 or 90° C. A stream of carbon dioxide gas was used to evaporate the water. The dried film was maintained at that temperature under a continuous flow of carbon dioxide for 30, 60 or 120 minutes. At the end of this time the mixture was rehydrated by addition of 1.0 mM HCl, dispersed for 10 seconds on a vortex stirrer, then either set aside for analysis or exposed to further dehydration-rehydration cycles up to seven times. The initial pH after the first cycle was 4.5 and this decreased stepwise to 2.8 at the end of 7 cycles. This pH range was chosen in order to protonate phosphate groups on the mononucleotides and thereby promote ester bond formation.

The first indication of RNA synthesis from AMP was the appearance of ionic current blockades detected by the nanopore instrument (FIG. 1). The blockade amplitude, duration and distribution resembled those expected for known polyadenylic acid homopolymers 40 nucleotides in length (Akeson, M., D. Branton, J. J. Kasianowicz, is E. Brandin, and D. W. Deamer. Biophys. J. 77, 3227 (1999)). Similar blockade patterns were also observed when UMP was used as a substrate. In our experience such blockades can only be produced by linear polyanions.

Example VIII

Analysis of Polymeric Products by RiboGreen Assays

Because the nanopore results indicated that small amounts of polymers were synthesized from mononucleotides in the presence of lipids, we were interested in determining yields, length of the polymers, and the nature of the chemical bonds linking the monomers. The RNA-like products were analyzed by performing RiboGreen assays (BioTek, Inc., Winooski, Vt.). This method was chosen as a general quantitative approach for two reasons. First, it is highly sensitive and gives useful estimates of nanogram to microgram quantities of RNA. The second reason is related to the complexity of the polymeric products. These are composed of RNA-like molecules having a broad range of chain lengths and variable amounts of 2'-5' and 3'-5' phosphodiester bonds within each molecule. For this reason, more commonly used methods such as HPLC and mass spectrometry could not be readily applied to analyze the products.

Figure 2:
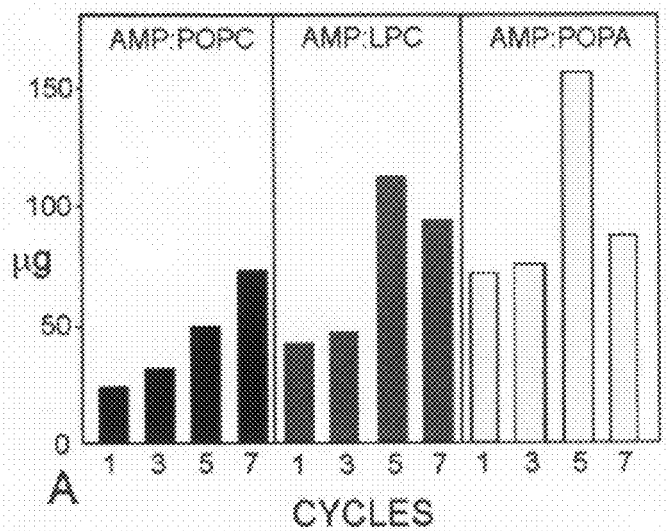
FIG. 2. Yields of RNA-like polymers obtained under different conditions. Experimental variables included the number of cycles and species of lipid (A), temperature (B) and mononucleotide:UMP, AMP and 1:1 mole ratio UMP:AMP mixture (C). Lanes labeled 0 in 2C represent mixtures of lipid vesicles and UMP or AMP that were dried at room temperature for 2 hours but not heated.
Figure 2:
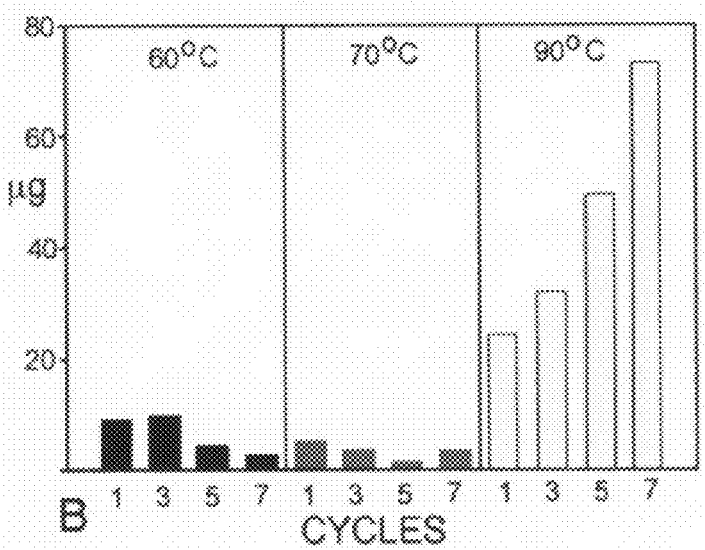
Figure 2:
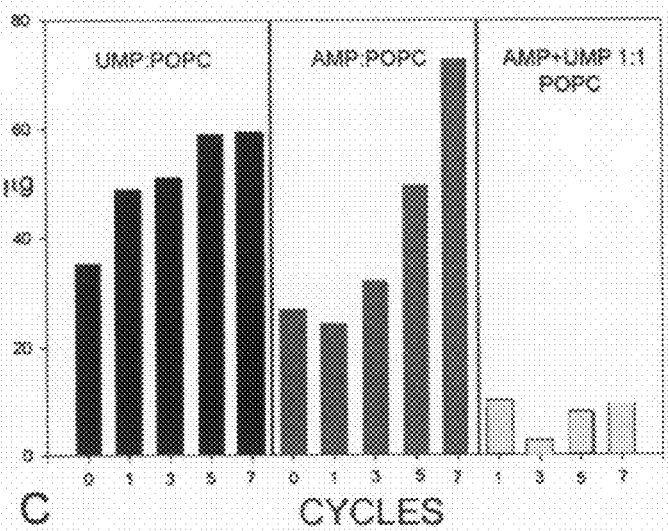

The total product ranged from 24 to 155 micrograms depending on the type of mononucleotide and the lipid composition used in the experiment (FIG. 2) with the higher amount equivalent to 1.5% yield of polymers by weight. Yields generally increased with the number of cycles the sample had experienced, reaching an apparent plateau after five cycles. Yields were highest when 1-palmitoyl-2-oleoylphosphatidic acid (POPA) was used (FIG. 2A), followed by lysophosphatidylcholine (LPC) and 1-palmitoyl-2-oleoylphosphatidylcholine (POPC). The yield obtained at 90° C. was significantly greater than at 60 and 70° C. (FIG. 2B). Comparison of a purine (AMP) and pyrimidine (UMP) mononucleotide showed similar yields. However, yields were markedly reduced in 1:1 mixtures of AMP and UMP (FIG. 2C). In this series we also detected small amounts of polymer synthesis if the mixture was dried under $CO_2$ in the absence of heating (FIG. 2C, lanes labeled 0).

Example IX

Analysis of Polymeric Products by Gel Electrophoresis

The results from nanopore analysis and RiboGreen assays were consistent with the possibility that linear strands of RNA-like polymers were synthesized in the presence of lipid. In order to confirm these observations and to determine the length of possible polymers, we used a procedure that produces radioactively labeled products for analysis by gel electrophoresis. The products were first treated with alkaline phosphatase to remove phosphate at the 5' end, then labeled with γ-[32P]ATP using T4 polynucleotide kinase and analyzed by denaturing polyacrylamide gel electrophoresis.

This experiment was run 74 times using a variety of controls and conditions, including the number of cycles, species of lipid and nucleotide, nucleotide-to-lipid ratio, temperature and RNase treatment. FIG. 3A shows one such series in which the number of cycles was varied, using AMP and 1-palmitoyl-2-oleoylphosphatidylcholine (POPC) in a 1:2 mole ratio. The amount of labeled RNA increased steadily over seven cycles, which was consistent with the indications of the RiboGreen assay (FIG. 2 A). Most of the RNA ranged from 25 to 75 nucleotides in length, with a smaller fraction in the 100 mer range. This range of chain length was apparent even after a single cycle, and subsequent cycles served to increase the amount of polymer, but not the chain length. The labeled polymers shown in the gels represent longer chains that could be precipitated in ethanol, only 1-2 percent of the total nucleotides initially present. The remainder, together with oligonucleotides shorter than 10 mers, were removed at this step in the procedure.

A series of controls is shown in the lanes labeled A-D. If air was used instead of carbon dioxide in seven drying cycles, much less labeled polymer was observed (lane. A). If the experiment was run for seven cycles in the absence of lipid (lane B) or if cycling was not carried out (lane C) yields of labeled product were undetectable Commercial polyadenylic acid was run as a positive control (lane D).

FIGS. 3B-F show the effect of several experimental variables on the lipid-dependent RNA synthesis reaction, which included temperature, substitution of different lipid and nucleotide species, and mixtures of nucleotides. Products could be detected by end-labeling for all three temperature ranges tested (FIG. 3B) with the highest yields at 90° C. All three lipids catalyzed the condensation reaction (FIG. 3C) but products were much reduced in the absence of lipid. The nucleotide to lipid ratio affected both chain length and apparent yield (FIG. 3D) with a ratio of 1:2 being optimal. Substituting UMP for AMP had little effect on the yield of polymer (FIG. 3E) but the resulting chain lengths were markedly reduced in a 1:1 mixture of AMP and UMP, perhaps because the mixed purine and pyrimidine nucleotides are less stabilized by stacking energy than the pure nucleotides.

We also tested whether RNase 1 could act on the products. RNase 1 is an exonuclease that produces a cyclic mononucleotide as a hydrolysis product and leaves a phosphorylated 5' end on the RNA substrate. In positive controls using synthetic homopolymers of polyadenylic acid and polyuridylic acid, RNase 1 clearly acted to reduce chain lengths (FIG. 4F). The commercial RNA homopolymers contain very long RNA molecules thousands of nucleotides in length, so that the homopolymers were not completely hydrolyzed during incubation with the enzyme but instead were reduced to shorter oligomers. The chain lengths of RNA-like products were not affected by the RNase, but the gel patterns were markedly enhanced compared to untreated products (FIG. 4F, last four lanes). Apparently the RNase 1 action exposed end groups on the products that were more readily end-labeled.

Figure 3:
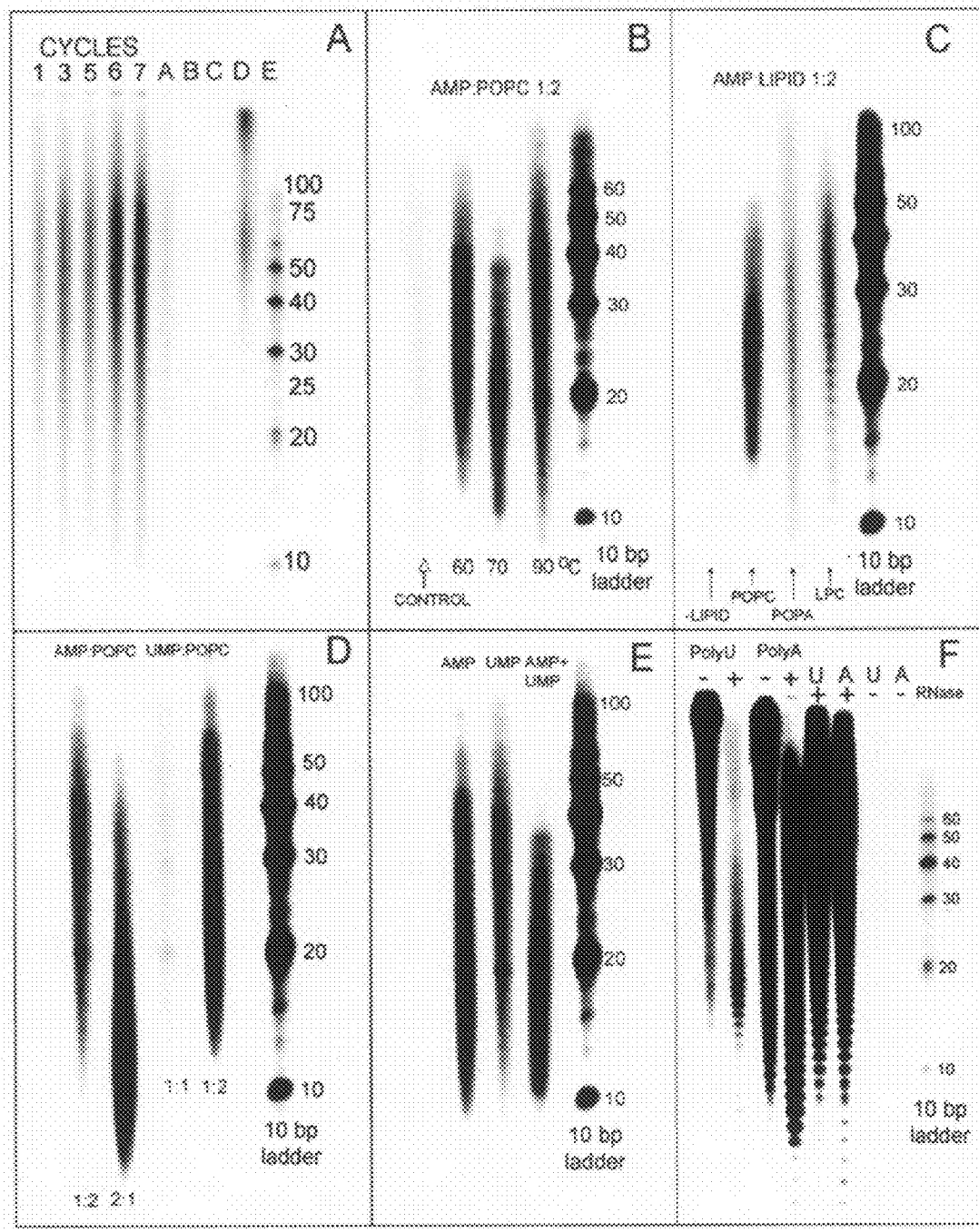
FIG. 3. Gel patterns of RNA-like products end-labeled with AT$^{32}$P.

Base-catalyzed hydrolysis (0.1 M NaOH, 10 minutes, 60 degrees) entirely hydrolyzed the RNA-like polymer to its component AMP or UMP monomers as indicated by thin layer chromatography (not shown). This result, taken together with the nanopore and electrophoresis results, confirmed that linear polymers of RNA were the primary product of the reaction, rather than branched products resulting from other kinds of covalent bond formation. Although we are confident that linear polymers are synthesized in the presence of lipid, it should be noted that the experimental conditions are much more complex than those of a typical chemical reaction. Each lane of reaction products shown in FIG. 3 represents a separate experiment, and during each wet-dry cycle there is a remixing of lipid, polymeric products and mononucleotide reactants. The reaction does not occur in solution, but instead in the interlamellar space of lipid lamellae in the dried film. This complexity leads to considerable variation of yield from one sample to the next, and also to variation in the chemical nature of the phosphodiester bonds (both 2'-5' and 3'-5' bonds are present) and the 5'-ends of the RNA.

Example X

Microscopic Appearance

Figure 4:
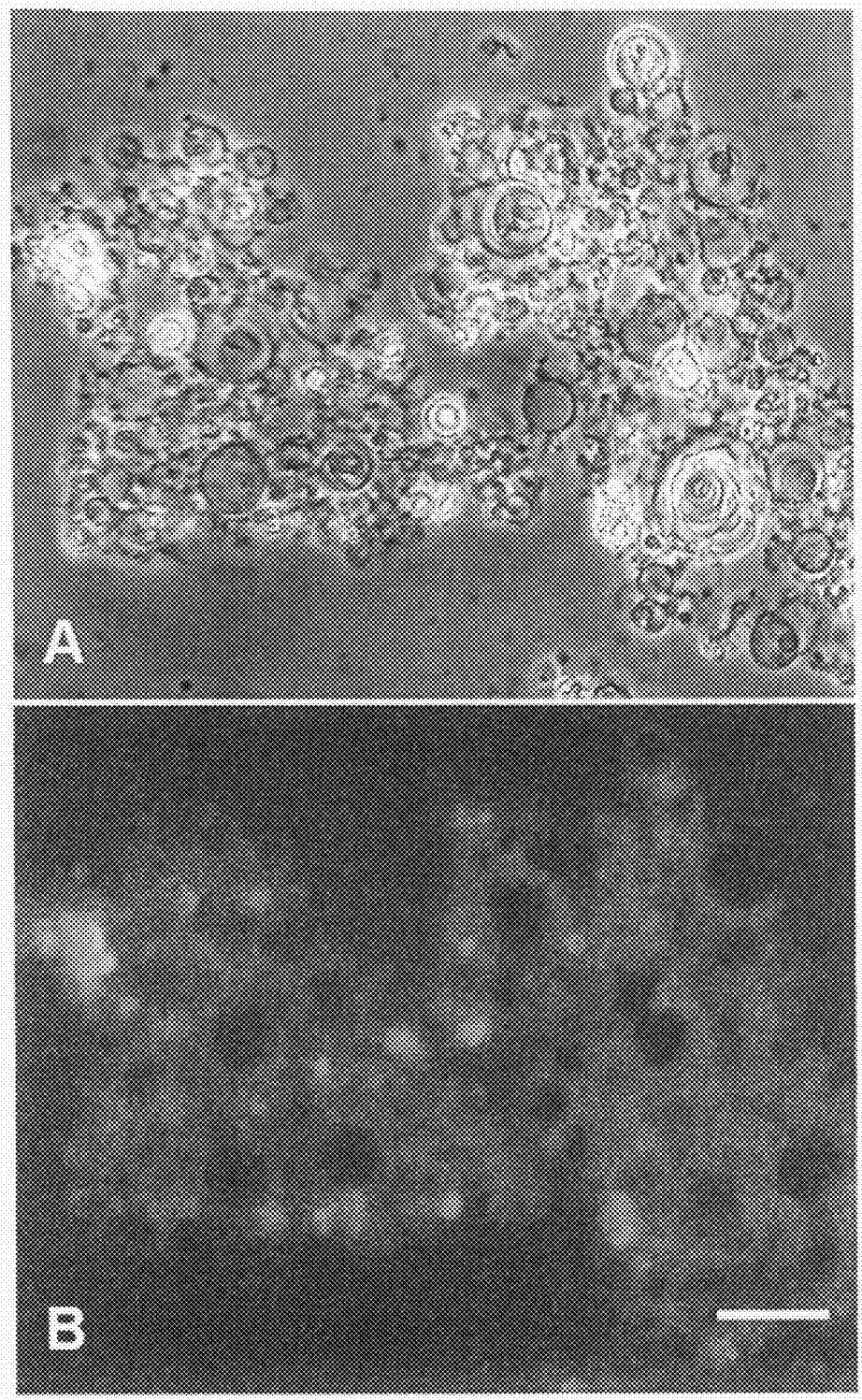
FIG. 4. Microscopic appearance of lipid structures visualized by phase (A) and fluorescence (B) microscopy. Bar shows 20 micrometers.

Membranous vesicles could be observed following rehydration after seven cycles of dehydration and heating at 90° C. A phase micrograph of such vesicles is shown in FIG. 4 A. The fact that vesicles are visible demonstrates that fusion has occurred during the drying cycles, because the original vesicles were in the sub-micron size range and would not be resolved by phase microscopy. The same preparation was stained with 0.1 mM ethidium bromide, which intercalates into RNA structures and produces a fluorescent stain of RNA that is present. FIG. 4 B shows a fluorescence image of the same sample. A diffuse fluorescence was pervasive, but some vesicles showed unstained interior volumes while others were brightly fluorescent. The presence of unstained vesicles lacking encapsulated material is predicted from the vesicle fusion that occurs during dehydration, because solutes are excluded from lamellar layers that were originally the interior of the lipid vesicles (Deamer, D. W. and G. L. Barchfeld. J. Mol. Evol. 18, 203 (1982)). We cannot be certain of the nature of the vesicles with higher content of fluorescently stained substances, but if long strands of RNA-like molecules are in fact present, it is possible that some of the products may accumulate in aggregates, rather then being dispersed throughout the lipid phase. Ethidium bromide staining produced virtually no fluorescence in control lipid samples that were dried and then rehydrated in the absence of RNA.

We noticed in the micrographs that vesicles after several cycles were somewhat disordered and aggregated, suggesting that partial degradation of the lipid was occurring. For this reason we followed the lipid composition by thin layer chromatography on silicic acid plates. The patterns clearly showed that after 7 cycles a fraction of the lipid had hydrolyzed to lysophosphatidylcholine (LPC) and fatty acids, which appeared as separate spots on the plate. Other experiments showed that LPC itself was not hydrolyzed by these conditions, and furthermore that pure LPC was able to promote polymer synthesis, as shown in FIGS. 2 and 3. For this reason acid-catalyzed hydrolysis of the lipid does not seem to be a factor in the reactions leading to polymer synthesis.

Example XI

Mechanism of Synthesis

The RNA-like polymers reported here differ from those of earlier studies in that the range of chain lengths is significantly longer (over 100 nucleotides) and the reaction does not require nucleotide activation to occur. The mechanism most likely involves an ordering effect of the lipid phase, presumably arising from the fact that the nucleotides are present at very high concentrations within lipid structures in the dry phase of each cycle. The combination of high concentration of reactants, interaction with polar head groups of lipids, and stacking of purine and pyrimidine bases would tend to align nucleotide molecules in such a way that phosphodiester bond formation is favored, with hydroxyl acting as a leaving group in the condensation reaction.

The low pH (~3) is also an important factor. Although the precise mechanism is not yet understood, it seems likely that at low pH ranges one of the —OH groups on the phosphate becomes protonated to —$OH_2^+$ which then becomes a potential leaving group. A neighboring 2' or 3' hydroxyl of a ribose then undergoes a nucleophilic attack on the phosphorous to produce an ester bond. The moderately elevated temperatures of 60-90° C. provide activation energy for the reaction without significant degradation of reactants or products.

It may be significant that, in contrast to the solid surface of a lamellar mineral such as clay, the lipid microenvironment is composed of fluid lipids. The diffusional mobility of mononucleotides adsorbed to a polar mineral surface would be markedly reduced, which would tend to slow reaction rates. However, reactant molecules captured within a fluid lipid matrix are able to diffuse and interact, which would promote covalent bond synthesis by condensation reactions. Another important difference between a multilamellar lipid phase and a solid bulk phase film of mononucleotides is that water molecules readily permeate lipid bilayers and therefore can be lost to the atmosphere, thereby reducing potential hydrolytic back reactions. In a solid bulk phase water molecules cannot readily diffuse away from the reaction site.

The fact that lysophosphatidylcholine (LPC) also promoted polymerization of mononucleotides suggested an interesting possibility. In designing the experiments, we assumed that the monomers would occur as 2-dimensional films between lipid bilayers. But LPC in dry or partially hydrated states forms a hexagonal I phase, in which the lipid molecules are arranged as cylinders around a central axis with head groups directed outward and tails inward (Stanley, W. M. Meth. Enzymol. 12, 404 (1968).). The term 'hexagonal' refers to the packing of the cylinders, which have an axis-to-axis spacing of 5 nm. In this structure, the mononucleotides would not occupy a 2-dimensional space, but instead would line up single file in the volume between the hexagonally packed cylinders. X-ray diffraction studies of lipid phases that have incorporated solutes during drying have not been carried out, particularly at elevated temperatures, but it seems possible that LPC and perhaps POPC and POPA exist in hexagonal phases when dried in the presence of solutes at elevated temperatures. This means that entrapped solutes such as AMP and UMP would be present as a one-dimensional linear array, which would further order the molecular aggregates and thereby promote polymerization by phosphodiester bond formation.

It is surprising that polymeric products are able to survive the conditions of the cycling used here to drive polymer synthesis. For instance, at pH 3 and 100° C., conditions similar to those used in our experiments, 10% of biological RNA in solution is hydrolyzed in 40 min (Stanley, W. M. Meth. Enzymol. 12, 404 (1968).). In control experiments in the absence of lipid and mononucleotides, we found that polyadenylic acid is in fact hydrolyzed to monomers and oligomers after several cycles. However, polyadenylic acid in the presence of lipid was less affected by these conditions, and after three cycles approximately 25% or the initial quantity remained. A certain amount of hydrolysis presumably does occur in the hydrated stage of a cycle, but when mononucleotides are present synthesis of phosphodiester linkages would also occur in the anhydrous stage, with the net effect of preserving longer polymers.

The polymeric products resemble biological RNA in that they are recognized by alkaline phosphatase and then by the T4 kinase enzyme that transfers phosphate from $AT^{32}P$ during end labeling. Treatment with RNase 1 did not hydrolyze the polymers, which was expected because of the presence of 2'-5' linkages that are not recognized by the enzyme. Surprisingly, RNase treatment often markedly improved the end labeling process, so that products that at first appeared only as faint bands on gels produced heavily labeled bands with clear ladders after RNA treatment (FIG. 3 F). This suggests that the RNA-like polymers have a variety of terminating groups, some of which are not recognized either by the alkaline phosphatase or the kinase enzymes Used for end labeling. RNase treatment apparently produces a more uniform array of end groups that are more readily labeled.

To summarize, lipid microenviroments are able to organize mononucleotides within a lipid matrix when phospholipid vesicles are mixed with mononucleotides and dried. Under these conditions, long strands of RNA-like molecules are synthesized non-enzymatically by a condensation reaction when the reactants are exposed to one or more cycles of dehydration and elevated temperatures, followed by rehydration. The chemical potential driving the reaction is presumably supplied by the anhydrous conditions, with heat providing activation energy. The hydroxyl of the 5' phosphate acts as a leaving group which then adds a proton from the medium to produce water. At the end of the reaction, the polymers are encapsulated in vesicles formed by the lipid upon rehydration. Polymer synthesis is achieved without chemical activation of the nucleotides.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A method of synthesizing a nucleic acid, said method comprising:
    (a) combining a mononucleotide composition and a lipid composition to produce a fluid reaction mixture;
    (b) drying said reaction mixture to produce a dried reaction mixture; and
    (c) rehydrating said reaction mixture;
    to produce a product comprising said nucleic acid.

2. The method according to claim 1, wherein said method comprises at least two iterations of said drying and rehydrating steps.

3. The method according to claim 1, wherein said nucleic acid is a ribonucleic acid.

4. The method according to claim 3, wherein said mononucleotide composition comprises ribonucleotides.

5. The method according to claim 4, wherein said ribonucleotides are chosen from adenosine 5'-monophosphate and uridine 5'-monophosphate.

6. The method according to claim 1, wherein said nucleic acid is a homopolymer.

7. The method according to claim 6, wherein said mononucleotide composition is a homogeneous mononucleotide composition.

8. The method according to claim 1, wherein said nucleic acid is a heteropolymer.

9. The method according to claim 8, wherein said mononucleotide composition comprises two or more different types of mononucleotides.

10. The method according to claim 1, wherein said mononucleotide composition and said lipid composition are combined in manner sufficient to provide for a mononucleotide to lipid molar ratio in said reaction mixture that ranges from 2:1 to 1:2.

11. The method according to claim 1, wherein said drying comprises subjecting said reaction mixture to a stream of dry gas.

12. The method according to claim 11, wherein said dry gas is carbon dioxide.

13. The method according to claim 1, wherein said rehydrating comprises contacting said dried reaction mixture with an aqueous fluid.

14. The method according to claim 13, wherein said aqueous fluid is an acidic fluid.

15. The method according to claim 14, wherein said acidic fluid is 1 mM HCl.

16. The method according to claim 1, wherein said method further comprises separating product nucleic acids from lipids.

17. The method according to claim 1, wherein said nucleic acid ranges in length from about 40 nt to about 100 nt or longer.

18. The method according to claim 1, wherein said nucleic acid is linear.

19. The method according to claim 1, wherein said method does not employ activated nucleotides.

20. A nucleic acid composition produced according to the method of claim 1, wherein said composition comprises nucleic acid polymers encapsulated in lipid vesicles and said nucleic acid polymers comprise 2'-5' linkages that are not recognized by RNase 1.

* * * * *